US006255504B1

(12) United States Patent
Roberts et al.

(10) Patent No.: US 6,255,504 B1
(45) Date of Patent: Jul. 3, 2001

(54) PROCESS FOR PREPARATION OF BRANCHED FATTY ACIDS

(75) Inventors: Glyn Roberts; Cornelis Martinus Lok; Christopher John Adams, all of Wirral; Kenneth Richard Seddon, Donaghadee; Martyn John Earle, Finaghy; Jennifer Therese Hamill, Belfast, all of (GB)

(73) Assignee: Unichema Chemie BV, Gouda (NL)

( * ) Notice: Subject to any disclaimer, the term of this patent is extended or adjusted under 35 U.S.C. 154(b) by 0 days.

(21) Appl. No.: 09/242,407

(22) PCT Filed: Jul. 7, 1997

(86) PCT No.: PCT/EP97/03642

§ 371 Date: Dec. 22, 1999

§ 102(e) Date: Dec. 22, 1999

(87) PCT Pub. No.: WO98/07680

PCT Pub. Date: Feb. 26, 1998

(30) Foreign Application Priority Data

Aug. 16, 1996 (EP) .................................. 96305982

(51) Int. Cl.$^7$ .................................................. C07C 51/00
(52) U.S. Cl. ........................................... 554/153; 554/150
(58) Field of Search ..................................... 554/153, 150

(56) References Cited

U.S. PATENT DOCUMENTS 3,090,807    5/1963    Illing et al. .

*Primary Examiner*—Deborah D. Carr
(74) *Attorney, Agent, or Firm*—Pillsbury Winthrop, LLP

(57) ABSTRACT

The invention relates to a process for the branching of fatty acids or derivatives thereof. More in particular, the invention provides a method for branching saturated fatty acids. This is achieved by contacting a source comprising fatty acids or derivatives thereof, with an ionic liquid. The invention also relates to the mixture of branched fatty acids so obtained.

18 Claims, No Drawings

PROCESS FOR PREPARATION OF BRANCHED FATTY ACIDS

This application is a 371 of PCT/EP97/03642 filed Jul. 7, 1997.

The present invention relates to a process for the branching of fatty acids or derivatives thereof. Said fatty acids or derivatives thereof may be saturated or unsaturated, short (C8) or long (C24) chain.

Fatty acids are versatile building blocks in various parts of the chemical industry, ranging from lubricants, polymers, solvents to cosmetics and much more. Fatty acids are generally obtained by hydrolysis of triglycerides of vegetable or animal origin. Naturally occurring triglycerides are esters of glycerol and generally straight chain, even numbered carboxylic acids, in size ranging from 8–24 carbon atoms. Most common are fatty acids having 12, 14, 16 or 18 carbon atoms. The fatty acids can either be saturated or contain one or more unsaturated bonds.

Long, straight chain saturated fatty acids (C10:0 and higher) are solid at room temperature, which makes them difficult to process in a number of applications. The unsaturated long chain fatty acids like e.g. oleic acid are liquid at room temperature, so easy to process, but are unstable because of the existence of a double bond. The branched fatty acids mimic the properties of the straight chain in many respects, however, they do not have the disadvantages associated with them. For example branched C18:0 (commercially known as isostearic acid) is liquid at room temperature, but is not as unstable as C18:1, due to the absence of unsaturated bonds. Branched fatty acids are therefore more desirable for many applications compared to straight chain fatty acids. For example, mixtures of branched fatty acids having 8 to 16 carbon atoms are frequently used in the lubricants industry.

Apart from branched fatty acids other fatty acid derivatives, such as oligomerised fatty acids, find use in similar and other applications. Oligomeric fatty acids refer to materials prepared by coupling of the monomer units, of which typically dimeric and trimeric species are desired building blocks in plastics, the personal care industry, lubricants, etcetera.

Conventionally, branched fatty acids are obtained by isomerisation of the straight chain, unsaturated fatty acids. The reaction can be carried out using a clay catalyst, and is generally performed at high temperature (e.g. 250° C.). A common process is the preparation of branched C18:0 (iso-stearic acid) from unsaturated straight chain C18:1 (or also C18:2).

These conventional processes suffer from a number of disadvantages. A first disadvantage is the fact that unsaturated fatty acids or the derivatives thereof can be converted to branched fatty acids, but saturated fatty acids (or derivatives) are usually not converted by the conventional processes. Hence, a source will be needed containing a relatively large concentration of unsaturated fatty acids, which limits flexibility. Although many sources of fatty acids contain unsaturated fatty acids together with saturated fatty acids, it is disadvantageous to separate the unsaturated from the saturated fractions due to high associated costs.

Although there are a number of sources available containing abundant unsaturated straight chain fatty acids, this relates predominantly to C18:1, C18:2, C18:3, and to a lesser extent C16:1. The smaller fatty acids C10, C12 and C14 do not occur widely in nature in an unsaturated, straight chain form. Thus, applying the conventional process for the preparation of the branched, saturated corresponding fatty acids (i.e. branched short chain fatty acids, C8–C16) is not possible from long chain (C18 and longer) fatty acids.

Yet a further disadvantage is that the current branching process as set out above is only possible using relatively high temperatures (at about 250° C.).

Hence, there is a need for a process for the preparation of branched fatty acids, in which these compounds are formed by branching/isomerisation of a source comprising fatty acids, which may be saturated or unsaturated, branched or straight chain or a mixture thereof. Also, there is a need for a process for the preparation of branched fatty acids having a chain length of 8 or more carbon atoms, but less than 18 carbon atoms.

It has now been found that the above objectives can be met by a process for the branching of fatty acids, wherein a source comprising fatty acids or derivatives thereof, is contacted with an ionic liquid.

An ionic liquid is herein to be understood as a salt (or a mixture of salts) in its liquid form (i.e. molten).

Since mixtures comprising both saturated fatty acids and unsaturated fatty acids can be converted, the process may suitably be employed using a source which contains both saturated and unsaturated fatty acids. Depending upon the availability and price of the source material, it is preferred that the source comprises at least 20%, but preferably more than 50% by weight of saturated fatty acids or derivatives thereof. It is also preferred that at least 50% by weight of said fatty acids or derivatives of fatty acids in the source material have a fatty acid chain length of between 8 and 24 carbon atoms. A preferred fatty acid in this respect is stearic acid or derivatives thereof.

Simple derivatives of fatty acids may be converted using the process according to the invention in a similar way as the fatty acids themselves. For some purposes, such derivatives may be preferred. Regarding such derivatives in the source as mentioned, esters are preferred, with alkylesters being the most preferred. Of these alkylesters, the most preferred ones are the fatty acid esters of alcohols having 1–4 carbon atoms, e.g. methanol, ethanol, propanol. Hence, a preferred source for performing the reaction according to the invention comprises stearic acid, methyl stearate, and/or ethyl stearate.

The above indicates that a source containing a wide variety of fatty acids (containing both saturated and unsaturated fatty acids, branched and straight chain fatty acids) can be converted. This one of the most surprising results and is a considerable advantage over the known processes. Yet a further advantage is that there is no need to carry out the reaction at elevated temperatures: as long as the temperature is high enough for the salt which is used as the reaction "solvent" (or medium) to be in its liquid form (i.e. molten).

With respect to the type of ionic liquid, a wide variety of possibilities exists. However, it will be clear that the preferred ionic liquids are the ones that are liquid at relatively low temperatures. Although some salts have very high melting points (i.e. common NaCl has a melting point of approx. 850° C.), there are salts known which melt under less severe conditions. An example of such salts are mixtures of two or more salts. In the case in which a mixture of two salts is used, the resulting ionic liquid is called a binary ionic liquid. Hence, it is preferred that in the process as set out above the ionic liquid comprises a binary ionic liquid.

Preferred binary ionic liquids comprise a metal(III) chloride and/or an organic halide salt, e.g. $[A]^+X^-$. Also, inorganic halide salts can be used. Suitable metal(III) chlorides include aluminium(III) chloride and iron(III) chloride. Regarding the organic halide, an unsymmetrical imidazolium or pyridinium halide has the advantage that isomerisation may now occur under mild conditions, contrary to conventional processes. A preferred unsymmetrical imidazolium halide is 1-methyl-3-ethylimidazolium chloride.

Oligomerisation can occur as a side reaction. Depending upon the operating temperature chosen, around 20–30% oligomerised products (mainly dimers and trimers) are formed, together with 40–60% long- and short chain branched fatty acids. Generally speaking, the higher the operating temperature, the more the balance shifts from branched fatty acids towards oligomerised fatty acids. Although oligomerised fatty acids, in particular dimers, are usefule products themselves, generally speaking the formation of branched fatty acids will be the primary objective.

Therefore, it is preferred that the process according to the invention is carried out at temperatures below 250° C. More preferred are operating temperatures of below 150° C., or even below 60° C., as long as the ionic liquid is chosen such that the mixture of ionic liquid and reactants is a liquid. Most preferred is an operating temperature of below 50° C.

As an additional advantage, there is no need for performing the reaction under increased pressure, and therefore, it is preferred for the reaction according to the invention to be carried out at atmospheric pressure.

Depending upon the intended use of the product, it is preferred that the product obtained using the process according to the invention comprises branched fatty acids having between 8 and 16 carbon atoms, preferably in an amount of at least 10% by weight based on the total amount of branched fatty acids. Therefore, another embodiment of the invention is a mixture comprising branched fatty acids, characterized in that at least 10%, or more preferably at least 30% by weight based on the total amount of branched fatty acids has between 8 and 16 carbon atoms.

In a practical set up, the process will be preferably be operated in a (semi-)continuous way, and the products separated from the reactants and ionic liquid.

The expensive unsymmetrical imadazolium or pyridinium halide can be easily separated from the product by extraction with solvents such as dichloromethane and hexane etc, or mixtures thereof. The imidazolium or pyridinium species can then be recycled following evaporation or distillation of the solvent.

The invention is further illustrated by the following examples, which are not to be interpreted as limiting the invention thereto.

EXAMPLE 1

Branching of Methyl Stearate

In a dry box, 1-ethyl-3-methylimadazolium chloride (3.55 g, 24.20 mmol) was added to doubly sublimed aluminium (III) chloride (6.45 g, 48.40 mmol) in a 100 cm$^3$ round bottomed flask, equipped with a dinitrogen inlet, Teflon stirrer bar and a stopper. The two solids were left to stand for 1 hour without stirring (to avoid excessive reaction rate and heat build up) until the melt had partially formed. The melt was then stirred for 3 hours until all the aluminium(III) chloride had reacted. The melt was transferred to a fume cupboard and connected to a supply of dinitrogen. Methyl stearate (3.00 g, 10.05 mmol, 30 w/w %) dissolved in dry cyclohexane was added dropwise, with a stream of dinitrogen to keep the air/moisture out. The cyclohexane was then removed by connecting the flask to a vacuum line (1 mmHg). After 0.5 h, the nitrogen was reconnected and the flask warmed to 85° C. with an oil bath. After about 95 mins the reaction was judged to be complete(i.e. no more methyl stearate observed by gas chromatography) and the reaction was quenched by the addition of water and crushed ice (50 cm$^3$) and the products were extracted with hexanes (4×30 cm$^3$ aliquots). The combined organic extracts were dried (MgSO$_4$), filtered and the solvent evaporated on a rotary evaporator. This gave 2.10 g of a colourless oil (72% of original weight. Remaining 28% is thought to be volatile compounds which are lost to the atmosphere. The products were separated into their different classes by Kugelrohr distillation at 1 mmHg pressure and analysed by gas chromatography, and the composition of the total resulting product (including volatiles) was:

| | |
|---|---|
| Volatiles | 28% |
| C7 & C8 methylisoalkanoates | 10% |
| C9–C14 methyl isoalkanoates | 13% |
| C16 & C18 methyl isoalkanoates | 20% |
| Dimer + Trimer + Polymer | 29% |

Total C7–C18 Branched fatty acids: 43%

EXAMPLE 2

Temperature Influence on Branching of Methyl Stearate

At different reaction temperatures, the same reaction as mentioned above under Example 1 has been performed. The only difference being that methyl stearate was added directly to the ionic liquid rather than being dissolved in cyclohexane (not necessary because reactions performed above the melting point of methyl stearate.

The results obtained are set out in table 1.

EXAMPLE 3

Branching of Stearic Acid

In a dry box, 1-ethyl-3-methylimidazolium chloride (3.55 g, 24.20 mmol) was added to doubly sublimed aluminium (III) chloride (6.45 g, 48.40 mmol) in a 100 cm$^3$ round bottomed flask, equipped with a dinitrogen inlet, Teflon stirrer bar and a stopper. The two solids were left to stand for 1 h without stirring (to avoid excessive reaction rate and heat build up) until the melt had partially formed. The melt was then stirred for 3 h until all the aluminium chloride had reacted. The melt was then transferred to a fume cupboard and connected to a supply of dinitrogen. Stearic acid powder (3.00 g, 10.54 mmol, 30w/w %) was added at room temperature with a stream of dinitrogen to keep air/moisture out. The stearic acid took approximately 10 mins to dissolve and there was an evolution of gas during the first 30 mins of the reaction. After 120 mins the reaction was judged to be complete (i.e. no more stearic acid observed by gas chromatography). The reaction was quenched by the addition of crushed ice (50 cm$^3$) and HCl (3 ml) and the products were extracted from the aqueous layer using 3×25 cm$^3$ aliquots of ethyl acetate. The combined organic extracts were dried (MgSO$_4$), filtered and the solvent evaporated on a rotary evaporator. This gave a yield of 2.67 g of a colourless oil (89% of original weight). The remaining 11% is due to volatile organic compounds lost to the atmosphere. The products were separated into their different classes by Kugelrohr distillation at 1 mmHg pressure. These fractions were then analysed by gas chromatography, and the composition of the total resulting product (including volatiles) was:

| | |
|---|---|
| Volatiles | 11% |
| C7–C9 branched fatty acids | 26% |
| C10–C15 branched fatty acids | 16% |
| C16–C18 branched fatty acids | 18% |
| Dimer + Trimer + Polymer | 29% |

It should be noted that the branched fatty acids contain low levels (<10%) of long chain hydrocarbons produced as a consequence of decarboxylation.

TABLE 1

Effect of temperature on reaction products of branching of methyl stearate.

| Temperature | Volatiles | C7–C14 methyl isoalkanoates | C16–C18 methyl iso. | Dimer + Trimer + polymer |
|---|---|---|---|---|
| 50–55° C. | 23.9 | <- - - - - - 54.7% - - - - - -> | | 21.4 |
| 59–62° C. | 28.8 | 11.4 | 35.8 | 24.0 |
| 68–75° C. | 16.0 | 11.8 | 42.6 | 29.6 |
| 120° C. | 24.1 | 9.4 | 36.0 | 30.5 |

What is claimed is:

1. Process for the preparation of branched fatty acids, wherein a source comprising fatty acids or derivatives thereof, is contacted with a molten salt or mixture of molten salts.

2. A method as claimed in claim 1, wherein the source comprises at least 20% by weight of saturated fatty acid or derivatives thereof.

3. Process according to claim 1, characterized in that the source comprises at least 50% by weight of fatty acids or derivatives thereof have a fatty acid chain length of between 8 and 24 carbon atoms.

4. Process according to claim 1, characterized in that the fatty acid derivative is an alkyl ester of a fatty acid.

5. Process according to claim 4, characterized in that the fatty acid derivative is an ester of fatty acid and an alcohol having 1–4 carbon atoms.

6. Process according to claim 1, characterized in that the molten salt or mixture of molten salts comprises a binary molten salt or mixture of molten salts.

7. Process according to claim 1, characterized in that the molten salt or mixture of molten salts comprises aluminum (III) chloride and/or an organic halide.

8. Process according to claim 7, characterised in that the organic halide is an unsymmetrical imidazolium halide or a pyridinium halide.

9. Process according to claim 8, characterized in that the unsymmetrical imidazolium halide is 1-methyl-3-ethylimidazolium chloride.

10. Process according to claim 1, characterized in that it is carried out at temperatures below 150° C.

11. Process according to claim 1, characterized in that it is carried out at atmospheric pressure.

12. Process according to claim 1, characterized in that the product obtained comprises branched fatty acids having between 8 and 16 carbon atoms.

13. Process according to claim 1 in which the products are separated from the reactants and molten salt or mixture of molten salts.

14. Process according to claim 13 in which the imadazolium or pyridinium halide is separated from the product/AlCl$_3$ adduct by extraction with a polar solvent.

15. Process according to claim 14 in which the product is liberated from the product/AlCl$_3$ adduct by hydrolysis in water.

16. Mixture comprising branched fatty acids, characterized in that at least 10% by weight based on the total amount of branched fatty acids has between 8 and 16 carbon atoms.

17. Process according to claim 2, characterized in that the source comprises more than 50% by weight of saturated fatty acids or derivatives thereof.

18. Process according to claim 1, characterized in that it is carried out at temperatures below 60° C.

* * * * *